United States Patent [19]

Grechishkin et al.

[11] 4,211,764

[45] Jul. 8, 1980

[54] GASTRIC SECRETION STIMULATION WITH 2-AMINO-5-(2-AMINOETHYL)-1,3,4-THIADIOZOLE

[75] Inventors: Leonid L. Grechishkin; Ljudmila K. Gavrovskaya; Vadim L. Goldfarb, all of Leningrad, U.S.S.R.

[73] Assignee: Nauchno-Issledovatelsky Institut Experimentalnoi Meditsiny, U.S.S.R.

[21] Appl. No.: 885,367

[22] Filed: Mar. 13, 1978

[51] Int. Cl.² .................... A61K 29/00; A61K 31/41; A61K 31/415
[52] U.S. Cl. ........................................ 424/9; 424/269; 548/138
[58] Field of Search .............. 424/269, 270, 9, 273 R; 260/302 D

[56] References Cited

PUBLICATIONS

Ohta et al., J. Pharm Soc. Japan, vol. 72, 1952, pp. 1636–1639.
Ohta et al., Chem Abs., vol. 47, 1953, pp. 9323–9324.

Primary Examiner—Anna P. Fagelson
Attorney, Agent, or Firm—Steinberg & Blake

[57] ABSTRACT

The proposed gastric secretion stimulator comprises an active principle which is 2-amino-5-(2-aminoethyl)-1,3,4-thiadiazole, and a pharmaceutical carrier for said active principle. The stimulator is used in the form of hydrochlorides. It displays a selective stimulating effect upon $H_2$-ceptors of secretory cells of the stomach and produces a maximum of gastric secretion, which is an important diagnostic factor. The gastric secretion stimulator of this invention is advantageous in that besides parenteral administration, it may be administered per os.

8 Claims, No Drawings

GASTRIC SECRETION STIMULATION WITH 2-AMINO-5-(2-AMINOETHYL)-1,3,4-THIADIOZOLE

FIELD OF THE INVENTION

The present invention relates to medicine and, more particularly, to selective gastric secretion stimulators. Gastric secretion stimulators are used to investigate the secretory function of the stomach and carry out diagnostic tests for different disorders, including hyperacid and subacid gastritis, gastric and duodenal ulcers, pernicious anemia, and stomach tumors.

BACKGROUND OF THE INVENTION

At present, the investigation of the secretory function of the stomach is carried out with the aid of either food or medicamental (chemical) stimulation. The food stimulation is both safe and convenient, but it cannot solve the basic diagnostic problem, i.e. to establish an adequate relationship between the functional state of the mucous membrane of the stomach and pathological-morphological changes therein, because there are a number of different internal and external factors, such as the quality and composition of food, the psychic state of the patient, and the situation in the laboratory during the gastric intubation, which affect the diagnosis. Besides, food stimulation does not make it possible to produce a maximum level of hydrochloric acid secretion in the stomach, which accounts for frequent diagnostic errors. In an attempt to solve the problem, chemical secretion stimulators were subsequently developed.

Today's chemical (medicamental) secretion stimulators include histamine, gastrin preparations (pentagastrin), and histalog (an analog of histamine). The selectivity of histamine is limited, so that in addition to gastric secretion, it produces a number of side effects in the patient, such as reddening of the skin, nausea, vomiting, headache, dizziness, bronchospasm, edema of the rima vocalis, hypotension, and shocks. In most cases, these side effects can be fully eliminated by introducing such traditional antihistamines as $H_1$-antagonists, including mepyramine, tavelgil and suprastin. For that reason, histamine is used for what is known as the histamine test only in hospitals and in a limited number of cases.

Pentagastrin is a synthetic analog of the gastrin hormone. As a rule, the first administration of pentagastrin brings about no complications. Taken in a sufficient dose, this preparation can produce a maximum level of secretion; however, being a polypeptide by nature, it can produce allergic and anaphylactic reactions as a result of repeated administrations. In addition, the effect of a single dose of this preparation does not last long, so that an objective assessment of a maximum hourly output of hydrochloric acid requires a prolonged drop phlebocylysis, which is only possible under hospital conditions. Another factor which somewhat limits the use of pentagastrin on a large scale is its comparatively high cost.

Of late, gastroenterologists have been increasingly interested in synthetic analogs of histamine, of which histalog (or betazol manufactured by Lilly of the United States) has found the most extensive application in clinical practice. Histalog is a pyrazole analog of histamine, i.e. 3-(5)-(2-aminoethyl)pyrazole. The intensity of its effect upon the cardiovascular system (hypotension) is 700 times as low as that of histamine, although histalog is only 70 times less effective than histamine as to its capability of stimulating gastric secretion. Parenteral administrations of histalog to humans in doses of 1 to 5 mg/kg result in a maximum secretory response of the stomach, whereas side effects are observed far less frequently than in the case of histamine, which accounts for an extensive clinical application of histalog (cf. C. E. Rosiere, M. J. Grossman, Science, 1951, 113, 651; J. B. Kirsner, W. L. Palmer, W. Ford, Gastroenterology, 1952, 20, 138; G. Feifel, W. Lorenz, A. Heimann, J. Wörsching, Klin. Wschr, 1972, 50, 422). It is not yet absolutely clear why histalog acts selectively upon the stomach. It is believed that apart from its selectivity as to receptors of the stomach, histalog can release endogenous histamine (cf. W. Lorenz, G. Feifel, A. Schmal, M. Hutel, E. Werle, Klin. Wschr., 1970, 48, 314).

Histamine is thought to act upon different physiological systems of the human organism through specific receptors (cf. A. S. Ash, H. O. Schild, Br. J. Pharmac., 1966, 27, 427–439; J. W. Black, W. A. Ducan, C. J. Durant, C. R. Ganellin, Nature, 1972, 236, 385–390). Experiments carried out by the abovementioned scientists revealed two types of histamine receptors, $H_1$ and $H_2$, in the human organism. It has been established that secretory cells of the stomach, which produce hydrochloric acid, are stimulated through $H_2$-receptors. Keeping in mind that histamine is equally selective both to $H_1$- and $H_2$-receptors, SKF of the United States have synthetized preparations which display a selective action upon $H_2$-receptors. These compounds can produce $H_2$-effects of histamine and, above all, gastric secretion, but with far less pronounced side effects on the part of $H_1$-receptors. These compounds are direct derivatives of histamine, more specifically, derivatives of 5-alkyl-4-(2-aminoethyl)imidazole. Experiments on animals indicate that pharmacologically, 5-methylhistamine appears to be the most promising under clinical conditions (cf. British Pat. No. 1,341,376, and French Pat. No. 2,254,311).

Experimental investigation of pharmacological properties of the foregoing compounds has been continued to this day (cf. G. Bertaccini, M. Impicciatore, T. Vitali, Farmaco. Ed. Sci., 1976, No 12, 935–938). However, no mention is made in medical literature of clinical uses of these compounds as diagnostic stimulators of gastric secretion, so that it is hard to assess their practical value. It must be pointed out that all the abovementioned chemical stimulators of gastric secretion, namely, histamine, pentagastrin, histalog and 5-methylhistamine have a major disadvantage in common: under clinical conditions, they can only be administered parenterally (intramuscular, intravenous and subcutaneous administration); if introduced per os, they are inactivated by the liver and enzymes of the alimentary canal, so that no secretory effect is produced. This factor hinders a large-scale application of said compounds because they have to be administered by means of painful injections which worry the patients. In addition, injections require sterile instruments and qualified staff.

SUMMARY OF THE INVENTION

It is an object of the present invention to provide a new gastric secretion stimulator producing a selective effect upon $H_2$-ceptors of secretory cells, devoid of the side effects of histamine and producing a maximum secretion level in the stomach when administered both parenterally and per os.

BRIEF DESCRIPTION OF THE INVENTION

The foregoing object is attained by providing a new gastric secretion stimulator comprising, according to the invention, an active principle which is 2-amino-5-(2-aminoethyl)-1,3,4-thiadiazole in the form of a pharmaceutically acceptable acid, and a pharmaceutical carrier for said active principle.

The carrier for the active principle is water (contained in ampoules for parenteral administration) or a pharmacologically neutral filler for tablets. The active principle content per parenteral injection or per os dose is 50 to 200 mg.

The preparation of this invention will be further referred to as thidazine.

Thidazine is a highly effective selective stimulator of gastric secretion and has a number of important advantages over the known preparations of a similar nature, such as histamine, histalog, 5-methylhistamine and pentagastrin. These advantages will become apparent from a consideration of the following detailed pharmacological and clinco-pharmacological description of thidazine.

DETAILED DESCRIPTION OF THE INVENTION

The detailed description of the present invention deals with pharmacological and clinical tests of thidazine with the active principle in the form of the hydrochloride.

The Effects of Thidazine Upon Gastric Secretion

While carrying out experiments on animals, the properties of thidazine were compared with those of histamine and histalog.

Chronic experiments were performed on male dogs weighing 20 to 25 kg and having a gastric fistula; prior to experiments, the animals were starved for 18 hours.

(a) intramuscular injections

Thidazine was introduced by means of intramuscular injections in increasing doses (0.05–0.08–0.1–0.2 mg/kg and more) through intervals of forty minutes until a maximum secretion level was reached. The gastric juice was analyzed for titratable acidity and proteolytic activity. The hydrochloric acid output was calculated in milliequivalents (mEq) and that of pepsin in milligrams. According to the experiments, thidazine can produce a maximum level of hydrochloric acid secretion in the stomach of a dog. In the case of intramuscular injections, the minimum active dose is 0.05 mg/kg, and the maximum dose is 3.0 mg/kg. The maximum hourly output of hydrochloric acid is 24 mEq per hour, while that of pepsin is 110 mg per hour. Similar doses of histamine dichloride or histalog were administered to control dogs. A total of 55 experiments were carried out, and the results, presented as cumulative dose-response curves, made it possible to compare the $pD_2$ values of the three preparations as related to $H_2$-ceptors; these values were as follows: histamine, 6.40; thidazine, 3.86; histalog, 3.63.

(b) administration per os

In the course of a special series of 20 experiments, thidazine was administered to dogs per os in a dose of 100 mg per head. After a latent period of 20 to 30 minutes, gastric secretion was brought about and reached a maximum level of 26 mEq per hour. Administration of histamine in doses of 10 and 20 mg, and histalog in doses of 50 and 100 mg produced no gastric secretion.

Thus thidazine can produce a maximum secretion in a dog's stomach when administered both parenterally and perorally. This is a vital distinction between thidazine on the one hand and histamine and histalog on the other.

Twenty acute Shay tests were performed on male rats weighing 250 to 300 g. The pylorus of each of the animals was ligated 2 hours before the slaughter. The pH and volume of the gastric juice were determined. Thidazine was administered to the control animals intraperitoneally in doses of 8 mg/kg. It was established that after the ligation of the pylorus, the administration of thidazine increased the output of hydrochloric acid more than threefold. In the control group, pH of the gastric juice was 2.2, and the average HCl output was 0.12 mEq per animal. In the experimental animals, pH of the gastric juice was 1.6, and the HCl output was 0.41 mEq.

The Effects of Thidazine On the Arterial Pressure

These experiments were performed on 11 cats weighing 2.5 to 4.0 kg and anesthetized with urethane-chlorazol mixture containing 60 mg/kg of chlorazol and 600 mg/kg of urethane. The arterial pressure was measured in the common carotid artery with the aid of a mercury pressure gauge. An intravenous injection of thidazine in a dose of 0.1 mg/kg brought the arterial pressure 30 mm of mercury below the original level. The same doses of histamine and histalog reduced the arterial pressure by 100 and 30 mm of mercury, respectively. No hypotensive reaction was observed with doses of thidazine below 0.1 mg/kg.

In a series of experiments of 18 rabbits weighing 2.5 to 3.5 kg, each having the common carotid artery in a cutaneous flap, the preparations were injected intravenously. In a dose of 0.1 mg/kg, thidazine reduced the arterial pressure by 12 mm of mercury; equimolar doses of histamine and histalog reduced the arterial pressure by 40 and 15 mm of mercury, respectively.

The Effects of Thidazine On $H_1$- and $H_2$-Receptors of Isolated Organs

Experiments were aimed at registering contractions of an isolated portion of the ileum of a guinea pig under the effects of increasing concentrations of thidazine, histamine and histalog; dose-response curves were plotted. According to the experiments, the $pD_2$ values in relation to $H_1$-receptors are as follows: histamine, 6.73; histalog, 4.23; thidazine, 3.4.

Contractions of an isolated horn of uterus of a rat due to the effect of acetylcholine in a concentration of $1.10^{-6}$ M were recorded on a paper tape. The experiments were aimed at establishing the degree to which the abovementioned preparations weaken such contractions. The effect of histamine was assumed to be equal to 100 percent. The relaxation effect of thidazine and histalog, due to their action upon $H_2$-receptors, was 15 and 16 percent, respectively.

Isolated auricles of guinea pigs were used to study the effects of thidazine upon $H_2$-receptors. Changes in the heart rate were measured, dose-response curves were plotted, and $pD_2$ values were calculated. The latter were as follows: histamine, 6.64; histalog, 4.80; thidazine, 5.10.

Experiments On Preventing the Effects of Thidazine By Blocking $H_1$- and $H_2$-Receptors Elimination of the effects upon $H_1$- and $H_2$-receptors was studied in experiments on 30 guinea pigs in which a shock was induced by an intravenous injection of thidazine in a dose of 190 mg/kg. A preliminary administration of an $H_1$-antagonist (tavegil) in a dose of 0.05 mg/kg prevented death in 90 percent of the cases.

In experiments on six dogs, a maximum level of gastric secretion was reached by means of intramuscular injections of thidazine in doses of 2 mg/kg. The secretory effect was completely prevented by a prior administration of an $H_2$-antagonist (methiamide) in a dose of 30 mg/kg.

In experiments on six cats, hypotension was caused by intravenous injections of thidazine in doses of 2 mg/kg. The hypotensive reaction was fully prevented by a prior administration of a combination of two histamine antagonists, namely, tavegil ($H_1$-receptors) and methiamide ($H_2$-receptors) in doses of 0.05 mg/kg and 40 mg/kg, respectively.

A special series of tests was aimed at studying the acute and chronic toxicity of thidazine, as well as its effects upon the functioning of different organs and systems of animals. The results of the tests are generalized in Table 1.

Table 1

| Serial No | Test | Results Control Period | Test Period |
|---|---|---|---|
| 1 | 2 | 3 | |
| A. | Acute Toxicity, $LD_{50}$ mg/kg | | |
| | Male mice, 18.0–21.0 g i/p | | 1.000 |
| | Male rats, 200–250 g i/p | | 1.000 |
| | Male guinea pigs, 280–350 g i/p | | 360 |
| | Male guinea pigs, 200–250 g i/v | | 190 |
| B. | Chronic Toxicity | | |
| | Male guinea pigs weighing 200–250 g | | |
| 1. | Daily intravenous injections of thidazine in doses 20 mg/kg (0.1.$LD_{50}$) during 10 days | | |
| | Average weight in control group, g | 230.8 ± 52 | 260.3 ± 51 |
| | Average weight in test group, g | 220.0 ± 58 | 252.3 ± 50 |
| 2. | Blood Analysis (at beginning and end of experiements) | | |
| | Hemoglobin, % Control group | 13.8 ± 0.4 | 11.9 ± 0.3 |
| | Test group | 11.8 ± 0.1 | 12.4 ± 0.3 |
| | Leukocytes, thous. Control group | 10920 ± 702 | 10070 ± 610 |
| | Test group | 11360 ± 900 | 9500 ± 835 |
| | Erythrocytes, mln. Control group | 3.79 ± 0.1 | 3.46 ± 0.1 |
| | Test group | 3.75 ± 0.1 | 3.93 ± 0.1 |
| | ESR, mm Test group | 2 | 2 |
| | Differential Blood Count | No significant changes | |
| | Coagulability of Blood | No changes | |
| 3. | ECG at beginning and end of experiment | No significant changes | |
| C. | Irritant Action of 1–5% Solutions On Bulbar Conjunctiva (guinea pigs, rabbits) intramuscular injection intravenous injection | | |
| | administration per os hypodermic injection | Negative reaction | |
| D. | Allergic Action (Arthus-Sakharov Phenomenon) Daily injections to male rabbits weighing 3.0 kg, during 6 to 7 days: test group, hypodermic injections of 0.1 ml of 1% solution | Negative reaction | |
| | control group, injections of 0.1 ml of normal horse serum | Necrosis, rejection | |
| E. | Effects on Depth and Rate of Respiration (rabbits and cats) | | |
| | 0.1–0.2 mg/kg i/v | | |
| | Respiration rate per minute | 90.0 ± 0.2 | 85.0 ± 0.4 |
| | Respiration amplitude, mm | 220 ± 0.3 | 180 ± 0.1 |
| | 0.1–0.2 mg/kg i/m | | |
| | Respiration rate per minute | 79.0 ± 2.0 | 78.0 ± 2.3 |
| | Respiration amplitude, mm | 160.0 ± 6.2 | 160 ± 10.1 |
| | 1 mg/kg i/v | | |
| | Respiration rate per minute | 120 ± 10.0 | 85.0 ± 6.0 |
| | Respiration amplitude, mm | 10.0 ± 0.8 | 14.0 ± 0.4 |
| | 2 mg/kg i/v | | |
| | Respiration rate per minute | 100.0 ± 8.0 | 85.0 ± 10.0 |
| | Respiration amplitude, mm | 110.0 ± 7.0 | 140 ± 20.0 |
| F. | Chronic Toxicity Three male dogs weighing 22 to 25 kg | | |
| 1. | Administration per os, 200 mg (in gelatin capsules), administration performed once a day during 10 days, one animal being | | |

Table 1-continued

| Serial No | Test | Results Control Period | Test Period |
|---|---|---|---|
| 1 | 2 | 3 | |
| | control | | |
| 2. | Behavior, food reflexes | No changes | |
| 3. | Weight prior to and after experiment | Unchanged | |
| 4. | Functions of Cardiovascular System | | |
| | (a) ECG at beginning and end of experiment | No significant changes | |
| | P - P, PQ, QRST, T | | |
| | (b) Phonocardiogram at beginning and end of experiment | No abnormalities in height and duration of sound; absolute synchronism with ECG | |
| | (c) Arterial Pressure at Beginning And End of Experiment | Fluctuations Within Physiological Norm, Between 110 and 140mm of Mercury | |
| 5. | Liver Functions | | |
| | (a) Bilirubin content, mg% | | |
| | at beginning of experiment | 0.15 | 0.16 |
| | 5th day of experiment | 0.15 | 0.15 |
| | 10th day of experiment | 0.15 | 0.15 |
| | (b) Glutamic-alanine transaminase content, units | | |
| | beginning of experiment | 28 | 30 |
| | 5th day of experiment | 34 | 30 |
| | 10th day of experiment | 35.5 | 32 |
| | (c) Mobility of serum proteins: | | |
| | (1) Corrosive Chloride Test | | |
| | at beginning of experiment | 1.0 | 1.0 |
| | 5th day of experiment | 1.0 | 1.0 |
| | 10th day of experiment | 1.0 | 1.1 |
| | (2) Thymol Test | | |
| | at beginning of experiment | 3 | 3 |
| | 5th day of experiment | 6 | 6 |
| | 10th day of experiment | 6 | 6 |
| 6. | Urinalysis: volume, specific weight, protein, microscopy of urinary sediment (dogs and guinea pigs; on day of analysis, water load was 5% of animal's weight) at beginning of experiment 5th day of experiment 10th day of experiment | No significant changes in diuresis and urine composition | |
| 7. | Histological Examination of Internal Organs (dogs, guinea pigs) on 10th day of experiment (microsections of liver, kidneys, adrenal glands and thyroid gland) | No microscopic changes, as compared to control | |

The pharmacological investigation of the effects of thidazine upon gastric secretion and the comparison of these effects with those of the known preparations enables one to draw the following conclusions:

1. Like histamine and histalog, thidazine can produce a maximum level of hydrochloric acid secretion in the stomach of an animal.

2. Unlike histamine and histalog, thidazine can produce a maximum secretory effect when administered both parenterally and per os; this is an important advantage of thidazine over the known preparations.

3. The comparison of the effects of thidazine upon $H_1$- and $H_2$-receptors of different objects indicates that the action of thidazine upon $H_2$-receptors is stronger than its action upon $H_1$-receptors. Thidazine is more selective than histalog.

4. When administered in doses sufficient to produce a maximum secretion level in a dog (3 mg/kg), thidazine produces no significant effect upon the arterial pressure, heart rate and general behavior of the animal. Thidazine is marked by a broad range of therapeutic action, as indicated by the following relationship:

$$\frac{LD_{50}}{ED_{50}} = \frac{1000}{8}.$$

The chronic toxicity tests, carried out on two different animal species, indicate that administered in doses of 1/10 $LD_{50}$, thidazine produces no significant effect upon the growth and development, as well as the blood composition of animals. Thidazine does not affect the functions of different internal organs and causes no pathological changes in the vital organs of animals.

As a preparation intended for diagnostic testing of the gastric secretion of healthy and diseased human beings, thidazine was clinically tested on 650 patients. The experiments were aimed at assessing the feasibility of performing a submaximum and maximum secretory test with both parenteral and per os administrations, and comparing the data obtained with the respective data for histamine and pentagastrin. Special attention was paid to side effects and the reproductibility of the secretory response after repeated administrations of the drug.

Some generalized clinical data is listed in Tables 2, 3, 4 and 5.

pentagstrin, thidazine can be administered per os, in the form of tablets or solutions introduced through a tube, as effectively as parenterally, by way of intramuscular or hypodermic injections. Thidazine makes it possible to carry out both submaximum and maximum secretory tests. The administration of thidazine is never followed by any significant side effects typical of the histamine test; therefore, it is unnecessary to introduce any anti- Table 2

Effects of Maximum Doses of Thidazine Upon Gastric Secretion of Patients of Middle Age Group

| Preparation | Number of observations | Hourly HCl output, milliequivalents per hour | | | HCl Concentration, milliequivalents per liter | | | Gastric Juice, ml per hour | | |
|---|---|---|---|---|---|---|---|---|---|---|
| | | 1st hour | 2nd hour | Δ% | 1st hour$^{(x)}$ | 2nd hour | Δ% | 1st hour$^{(x)}$ | 2nd hour | Δ% |
| Thidazine (per os, 2mg/kg) | 13 | 4.3 | 21.6 | +402.3 | 33.3 | 103.2 | +209.9 | 102.1 | 227.9 | +123 |
| Thidazine (hypodermic, 2mg/kg) | 11 | 8.2 | 18.3 | +471.9 | 43.9 | 100.8 | +129.6 | 87.0 | 200.5 | +130.5 |
| Pentagastrin (6 mg/kg) | 15 | 3.7 | 16.5 | +345.9 | 35.3 | 94.0 | +166.3 | 106.3 | 174.0 | +63.7 |

$^{(x)}$1st hour of test (basal secretion)
2nd hour of test (secretion in response to administration of drug)

Table 3

Comparison of Gastric Secretion Characteristics for 20 Patients: 1.5 mg/kg Parenteral Doses of Thidazine and Simple Histamine Test (0.01 mg/kg)

| Characteristics: | Total Acidity, units | | Free Acidity, units | | HCl Output, milliequivalents per hour | | Peak HCl Output, milliequivalents | | Stimulated Total Acidity-Basal Acidity Ratio | |
|---|---|---|---|---|---|---|---|---|---|---|
| | Histamine | Thidazine | Histamine | Thidazine | Histamine | Thidazine | Histamine | Thidazine | Histamine | Thidazine |
| | 92.0+23 >0.05 | 90.3+22 | 81.7+21 >0.05 | 77.0+20 | 12+0.4 >0.05 | 12.2+0.7 | 8.8+0.2 >0.05 | 8.9+0.3 | 2.52+0.12 >0.05 | 2.54+0.09 |

Table 4

Reproducibility of Secretory Response to Introduction of Thidazine and Histamine with Reference to Total Acidity Values (each group of patients includes 10 persons)

| | Thidazine | | | Histamine |
|---|---|---|---|---|
| Values | Dosage 1.5mg/kg per os | 0.7 mg/kg hypodermic | Basal Secretion | 0.01 mg/kg hypodermic |
| % of difference$^{(x)}$ (fluctuations) | 0–22 | 15–42 | 0–62 | 0–53 |
| Average difference, % | 7.5 | 31 | 42 | 33 |

$^{(x)}$Percentage of difference is the relationship of the difference between the total acidity values registered in the first and second tests of a patient to the greater of these values.

histamine preparations in advance. The per os administration of thidazine is simple and convenient and can be practiced in outpatient clinics.

Thus the clinical observations corroborate the experimental data, wherefore it can be stated that thidazine is a selective stimulator of gastric secretion almost devoid of side effects; it can also be stated that thidazine has a number of important advantages over the prior-art preparations used for the same purpose (histamine and gastrin); the most important features of thidazine are as follows: it may be administered per os, and it is highly selective, safe and convenient for use under clinical conditions. The clinical investigation also helped to determine effective doses of the proposed preparation Table 5

Comparative Effects of Thidazine, Histamine and Pentagastrin Upon Main Gastric Secretion Characteristics of Patients With Duodenal Ulceration

| Secretion Characteristics | Thidazine | | Histamine | | Pentagastrin | |
|---|---|---|---|---|---|---|
| | 1st hour$^{(x)}$ | 2nd hour | 1st hour$^{(x)}$ | 2nd hour | 1st hour$^{(x)}$ | 2nd hour |
| Milliequivalents per hour | 7.25 ± 0.9 | 23.9 ± 1.8 | 7.0 ± 1.2 | 19.4 ± 1.6 | 7.4 ± 0.8 | 24.8 ± 1.5 |
| Pep/sin Output, units per hour | 4.0 ± 0.7 | 17.8 ± 2.3 | 3.7 ± 1.2 | 4.8 ± 3.0 | 3.3 ± 0.8 | 19.3 ± 3.8 |
| Chymosin Output, units per hour | 17.3 ± 0.3 | 218.2 ± 4.0 | 16.0 ± 0.008 | 16.4 ± 0.04 | 157.3 ± 5.9 | |

$^{(x)}$first hour: basal secretion

The clinical observations show that in adequate doses, in its secretory activity, thidazine is close to histamine and pentagastrin. However, unlike histamine and pentagastrin, thidazine is close to hista- for submaximum and maximum tests and different forms of administration. The effective dosage data is listed in Table 6.

Table 6

| A. Doses for Submaximum Secretion Tests | | | |
|---|---|---|---|
| Mode of administration | Histamine dichloride mg/kg | Histalog (betazol) mg/kg | Thidazine mg/kg |
| Hypodermic or intramuscular | 0.008 | 0.9 | 0.8 |
| Per os | — | — | 1.5 |

| B. Doses for Maximum Secretion Tests | | | |
|---|---|---|---|
| Mode of administration | Histamine dichloride mg/kg | Histalog (betazol) mg/kg | Thidazine mg/kg |
| Hypodermic or intramuscular | 0.025 | 1.7 | 1.6 |
| Per os | — | — | 2.0 |

The active principle of the proposed preparation, namely, 2-amino-5-(2-aminoethyl)-1,3,4-thiadiazole of the formula:

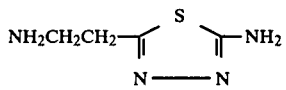

is a compound that has been described in literature (cf. Masaki Onta, J. Pharm. Soc. Japan, 72, 1636/1952/). The dichlorohydrate of this compound is white-yellowish crystalline powder. It has a poor hygroscopicity and a melting point of 238° C., the melting being accompanied by decomposition (according to literature, the melting point is 237° C., the melting being accompanied by decomposition). The powder is readily soluble in water; its aqueous solution is transparent, colorless and stable over prolonged periods of time. Solution of this compound in 0.01 M of hydrochloric acid at a concentration of $10^{-4}$ M has a characteristic absorption spectrum in the UV range with a maximum of $245 \pm \pm 1$ nanometers.

EXAMPLE 1

The preparation of di- and monohydrochlorides of 2-amino-5-(2-amino-ethyl)-1,3,4-thiadizole.

(a) Preparation of 2-amino-5-(2-phthalimidoethyl)-1,3,4-thiadiazole.

22 g of 1-(2-phthalimidopropionyl)thiosemicarbazide is dissolved, with stirring, in 45 ml of 96% of sulfuric acid. The solution is warmed at 100° C. for 5 to 10 minutes, whereupon it is cooled, stirred and poured on crushed ice, after which it is neutralized with 20% solution of sodium hydroxide until pH is 8 to 9. The precipitate is filtered and washed with water on the filter in order to completely remove inorganic salts. The yield of the product is 18.5 g (90% of the theoretical); the melting point of the product is 229°–231° C. (with decomposition from hydrous dioxane). According to literature, the melting point is 226°–227° C.

Found: C, 52.31; H, 3.82; N, 20.24; S, 11.67. $C_{12}H_{10}N_4O_2S$; requires: C, 52.54; H, 3.67; N, 20.43; S, 11.69.

The initial compound, 1-(2-phthalimidoproprionyl) thiosemicarbazide may be prepared as described in literature (cf. C. Ainsworth, R. J. Jones, J. Am. Soc., 81,1643/1953/).

(b) The preparation of dihydrochloride of 2-amino-5-(2-aminoethyl)-1,3,4-thiadiazole.

17.8 g of 2-amino-5-(2-phthalimidoethyl)-1,3,4-thiadiazole, 3.25 ml of hydrazine hydrate and 130 ml of alcohol are heated during 3 hours at a boiling temperature. The alcohol is heated during 3 hours at a boiling temperature. The alcohol is evaporated in vacuum; 150 ml of water and 25 ml of a 20% hydrochloric acid are added to the remainder; the mixture is warmed for 30 minutes and cooled; the precipitated phthalhydrazide is filtered and washed with water on the filter. The aqueous solution is evaporated in a steam bath, dissolved in 70 ml of cool water, treated with neutral activated carbon, and filtered. The filtrate is evaporated in a steam bath to complete dryness. The yield is 14 g (100% of the theoretical); the melting point of the product is 238° C. (with decomposition from water-methanolacetone). According to literature, the melting point is 237° C. (with decomposition).

Found: C, 22.03; H, 4.64; N, 25.81; S, 15.00; Cl, 32.25. For $C_4H_8N_4S \cdot 2HCl$; requires: C, 22.13; H, 4.64; N, 25.80; S, 14.77; Cl, 32.66.

(c) The preparation of monochlorohydrate of 2-amino-5-(2-aminoethyl)-1,3,4-thiadiazole.

0.8 ml of distilled triethyl amine is added to a suspension of 1.09 g of dihydrochloride of 2-amino-5-(2-aminoethyl)-1,3,4-thiadiazole in 10 ml of absolute alcohol. The mixture is stirred during 60 minutes, whereupon the precipitate is filtered and washed with alcohol. The yield is 0.9 g (100% of the theoretical); the melting point of the product is 202°–203° C.

Found: Cl 19.26. $C_4H_8N_4S \cdot HCl$, requires Cl 19.63.

EXAMPLE 2

The preparation of solutions of 2-amino-5-(2-aminoethyl)-1,3,4-thiadiazole for injection or per os administration.

The preparation is used in the form of 5% aqueous solution in an amount of 0.8 to 2 mg/kg; this applies to hypodermic or intramuscular injections. As regards per os administration, the preparation is taken in an amount of 1.5 to 2.0 mg/kg.

Solutions of dihydrochloride of 2-amino-5-(2-aminoethyl)-1,3,4-thiadiazole display a strongly acidic reaction, for which reason the solution is neutralized in advance with sodium hydroxide to reach a pH level of 6 to 7, which means that the compound is transformed into a monohydrochloride.

To produce 1 l of 5% solution of the preparation, 5 g of dichlorohydrate of 2-amino-5-(2-aminoethyl)-1,3,4-thiadiazole is dissolved in 900 ml of water for injection; 30% solution of sodium hydroxide is added to reach a pH level of 6 to 7; water is then added so that the total volume is 1 l. The solution is filtered and poured into ampoules of neutral glass, each containing 1 ml, which are sterilized with steam at 100° C. during 30 minutes.

In order to establish the authenticity of the preparation, use is made of the reaction between a hot solution of the preparation in hydrochloric acid and sodium nitrite (the reduction of nitrite ions registered by an iodine-starch indicator); use can also be made of a positive reaction to ions of chlorine.

The authenticity of the preparation can also be established with reference to the characteristic UV spectrum with a maximum absorption at $245 \pm 1$ nanometers.

The quantitative determination can be performed spectrophotometrically, by measuring the optical density of the solution, or by titrometrically registering ions of chlorine.

The ampoules must be stored in dark places.

EXAMPLE 3

The preparation of tablets.

To produce a 0.15 g tablet, 0.05 g of dihydrochloride of 2-amino-5-(2-amino-ethyl)-1,3,4-thiadiazole is mixed with the filler and tableted. The composition of the filler is as follows: sugar, 0.0535 g; starch, 0.0425 g; talcum, 0.003 g; calcium stearate, 0.001 g. The authenticity test and quantitative determination are performed as in Example 2. The tablets must be stored in dry places.

What is claimed is:

1. Gastric secretion stimulator composition, comprising a gastric secretion stimulating effective amount of a salt of 2-amino-5-(2-amino-ethyl)-1,3,4thiadiazole of a pharmaceutically acceptible acid, and a pharmaceutical carrier therefor.

2. The gastric stimulator of claim 1, wherein said pharmaceutical carrier is water.

3. The gastric stimulator of claim 1, wherein said pharmaceutical carrier is a mixture of pharmaceutically acceptible solid fillers.

4. The gastric stimulator of claim 1, wherein said salt is present in an amount of 50 mg/ml per parenteral injection.

5. The gastric stimulator of claim 1, wherein said composition is a tablet and said salt is present in an amount of 0.05 g per tablet.

6. Method for stimulating gastric secretion, which comprises administering to a patient requiring the same a gastric secretion stimulating effective amount of a salt of 2-amino-5-(2-amino-ethyl)-1,3,4-thiadiazole of a pharmaceutically acceptible acid.

7. The method of claim 6 wherein the mode of administration is parenteral.

8. The method of claim 6 wherein the mode of administration is per os.